United States Patent
Werblin et al.

[11] Patent Number: 5,968,094
[45] Date of Patent: Oct. 19, 1999

[54] COMPOUND INTRAOCULAR LENS

[75] Inventors: Theodore P. Werblin, Princeton, Wash.; Tadmor Shalon, St. Louis, Mo.; James E. Roberts, Laguna Niguel, Calif.

[73] Assignee: Emmetropia, Inc., Princeton, W. Va.

[21] Appl. No.: 08/916,426

[22] Filed: Aug. 22, 1997

Related U.S. Application Data

[63] Continuation of application No. 08/529,614, Sep. 18, 1995, abandoned.

[51] Int. Cl.$^6$ ........................................................ A61F 2/16
[52] U.S. Cl. ...................................................... 623/6; 623/4
[58] Field of Search ............................................. 623/6, 4

[56] References Cited

U.S. PATENT DOCUMENTS

| | | | |
|---|---|---|---|
| 4,240,163 | 12/1980 | Galin | 623/6 |
| 4,636,212 | 1/1987 | Posin et al. | 623/6 |
| 4,655,770 | 4/1987 | Gupta et al. | 623/6 |
| 4,769,035 | 9/1988 | Kelman | 623/6 |
| 4,932,971 | 6/1990 | Kelman | 623/6 |
| 5,098,444 | 3/1992 | Feaster | 623/6 |
| 5,171,267 | 12/1992 | Ratner et al. | 623/6 |
| 5,366,502 | 11/1994 | Patel | 623/6 |

FOREIGN PATENT DOCUMENTS

| | | | |
|---|---|---|---|
| 2666735 | 3/1992 | France | 623/6 |
| 9220302 | 11/1992 | WIPO | 623/6 |

*Primary Examiner*—David J. Isabella
*Assistant Examiner*—Dinh X. Nguyen
*Attorney, Agent, or Firm*—Arent Fox Kintner Plotkin & Kahn, PLLC

[57] ABSTRACT

The compound intraocular lens ("CIOL") of the present invention includes a preexisting lens within the eye (which can be either of the crystalline lens of the eye, a conventional IOL or a base lens of a multi-component IOL) used as a platform for support (i.e., the "support lens") a cap situated on the support lens, and a sandwich lens which is sandwiched between the support lens and the cap lens. Utilizing a pre-existing implanted IOL or the crystalline lens of the eye, a surgeon can modify a patient's vision characteristics merely by utilizing the cap and sandwich lenses in conjunction with the pre-existing implanted IOL or the crystalline lens of the eye. The CIOL has several enhanced features: (1) it can be configured as a monofocal, multi-focal, tri-focal or bifocal optical system; (2) it can be configured to correct astigmatism, if desired; (3) it can be comprised of ultraviolet light-absorbing material; (4) it can be comprised of tinted materials if desired; and (5) the components may be comprised of chemically-treated materials to decrease their cellular reactivity.

62 Claims, 19 Drawing Sheets

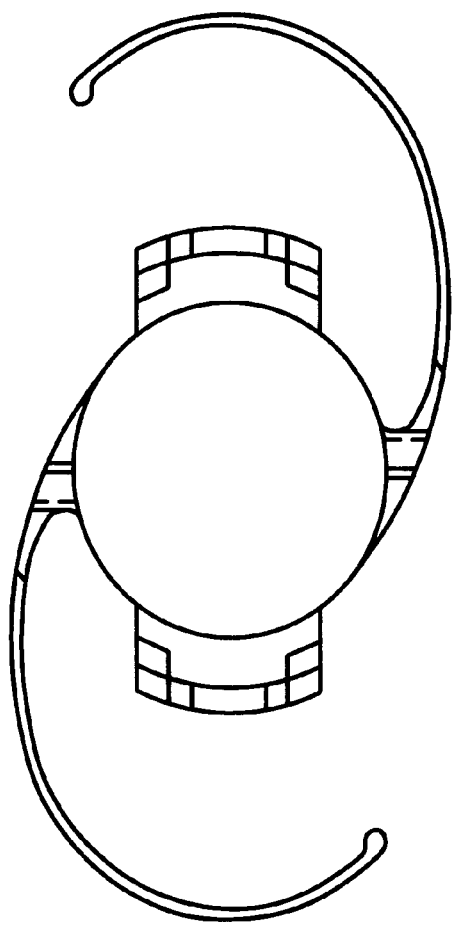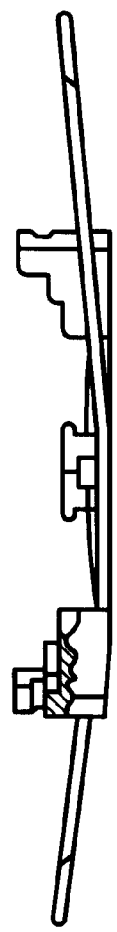

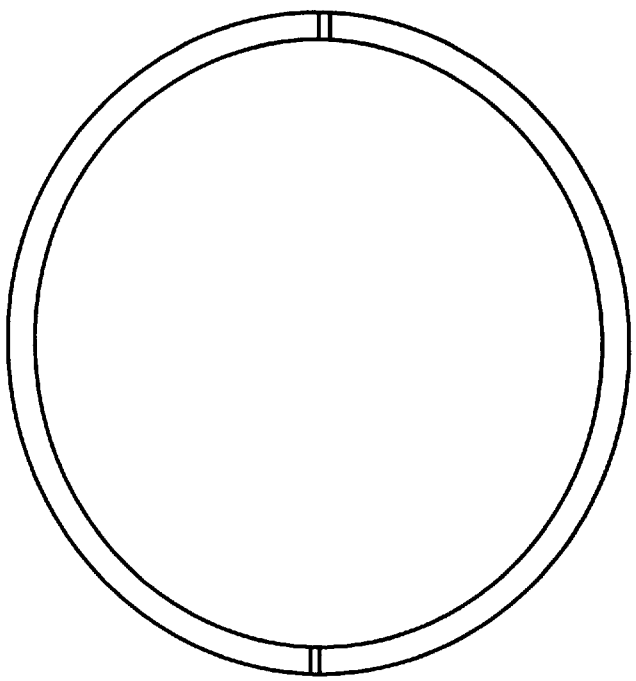

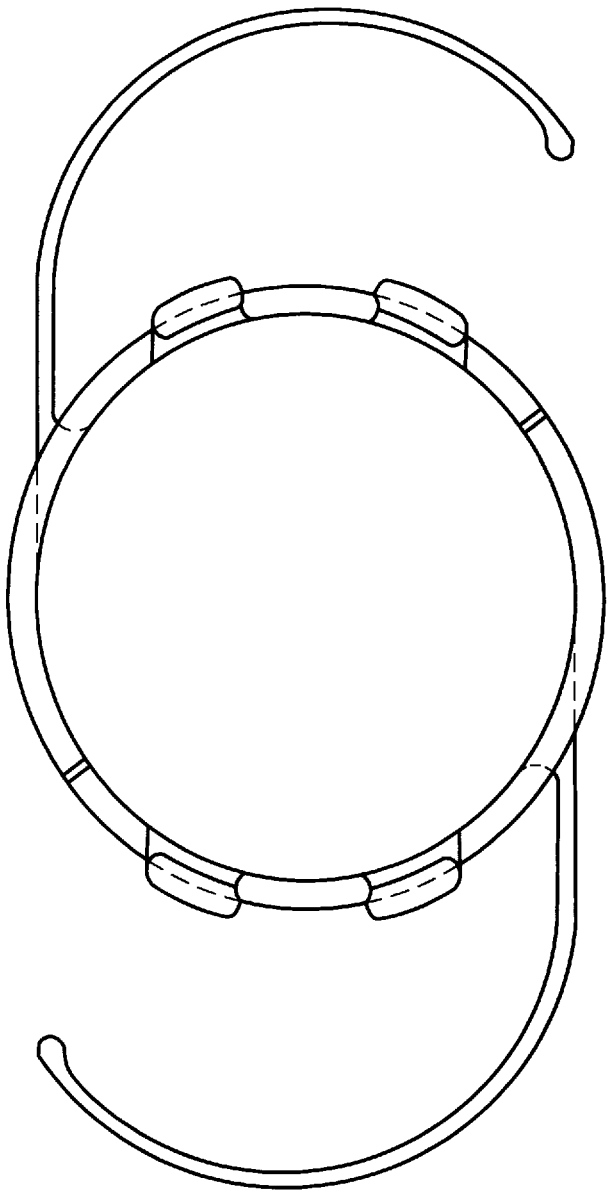
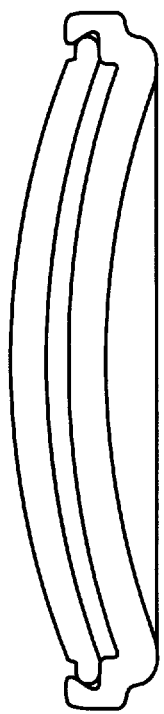
FIG.8A
FIG.8B

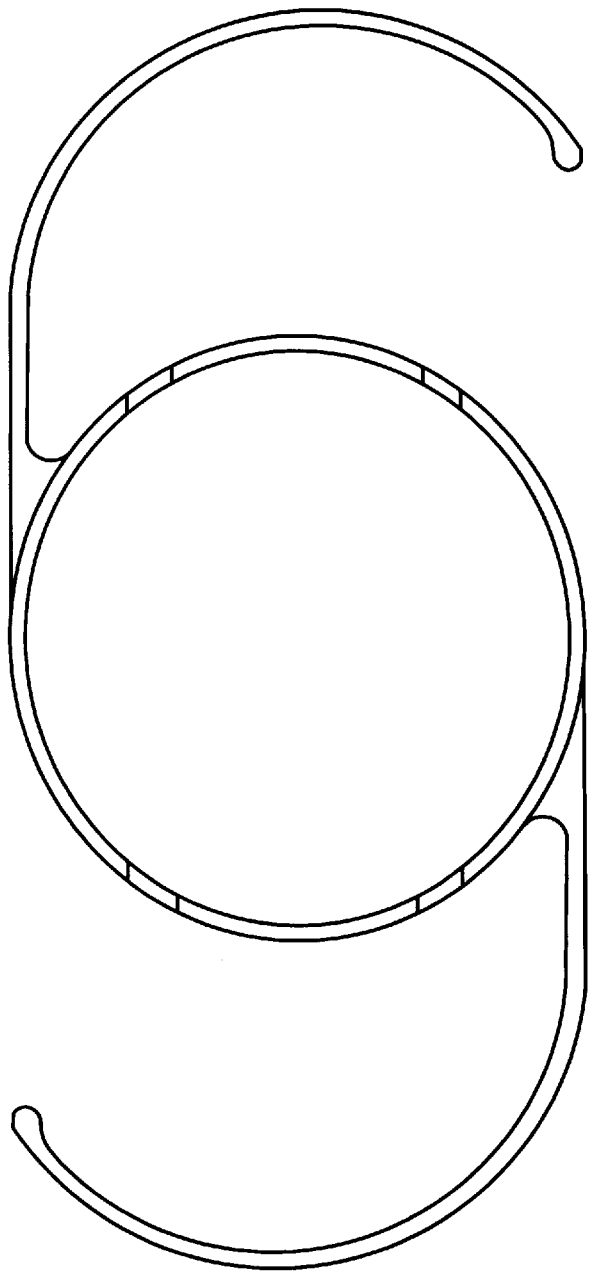
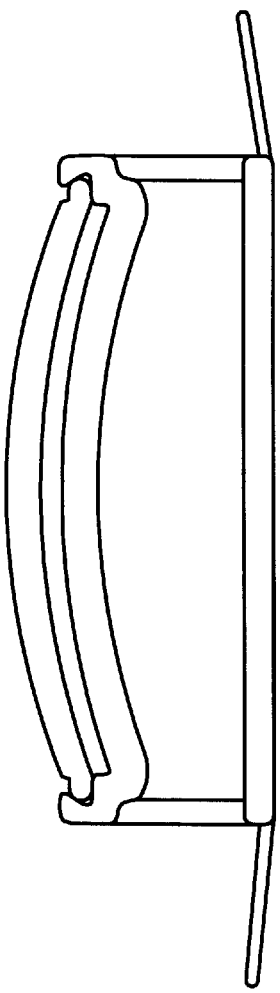
FIG.9A
FIG.9B

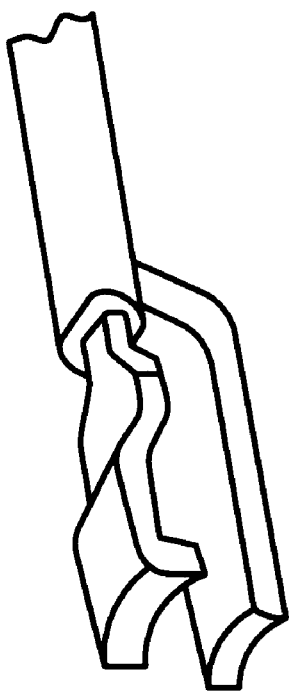
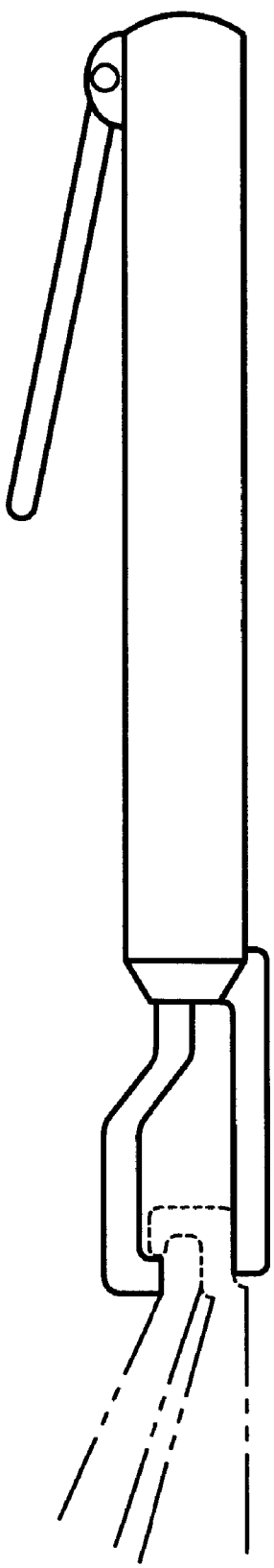
FIG. 21
FIG. 21A

COMPOUND INTRAOCULAR LENS

This application is a continuation of application Ser. No. 08/529,614, filed Sep. 18, 1995, now abandoned.

BACKGROUND OF THE INVENTION

The present invention relates to a compound intraocular lens ("CIOL") for an eye.

During the last several decades, there has been a tremendous evolution of technology and an escalation of interest in refractive surgery for the eye. The most commonly performed refractive surgical procedure, cataract extraction with intraocular lens implantation, as well as more recently popularized corneal refractive surgical procedures, have a number of drawbacks and limitations. The lack of postoperative refractive accuracy vis-a-vis glasses and/or contact lenses is a common problem and is seen in all of these techniques. Those factors affecting the accuracy of IOL surgery include wound-induced or pre-existing astigmatism, anterior chamber depth and axial length measurement error.

A lack of refractive stability further complicates all known corneal procedures. Surgeons agree that the desired outcome of refractive surgery is to allow the patient to see without external correction with vision acuity approximately equivalent to the level the patient had with correction prior to surgery. Therefore, the refractive endpoint must hover between 20/20 and 20/25 uncorrected acuity in 95–99% of cases. Currently, the refractive accuracy of both IOL and corneal procedures falls significantly short of this goal. See Werblin, T. P. and Stafford, G. M., "The Casebeer System for Predictable Corneal Refractive Surgery. One Year Evaluation of 211 Consecutive Patients," Vol. 100 *Ophthalmology* at 1095–1102 (1993); Holladay, J. T. and Prager, T. C., et al., "Improving the Predictability of Intraocular Lens Power Calculations," Vol. 104 *Arch Ophthalmology* at 539–541 (1988); Werblin, M.D., Ph.D., T. P., "Should We Consider Clear Lens Extraction for Routine Refractive Surgery," Vol. 8 *Journal of Refractive & Corneal Surgery* at 480–81 (November/December 1992). These procedures have accuracy rates of +/−0.5 D to 1.0 D, resulting in 95–99% of patients postoperatively achieving 20/40 or better uncorrected vision. The goal of 20/25 or better uncorrected vision can be achieved only if the standard deviation of the refractive procedure is +/−0.25 D, at least twice the accuracy of any existing refractive surgical procedure.

Moreover, in traditional intraocular lens applications, the lens cannot be modified or enhanced once in place in the eye. The ability to fine-tune or enhance radial keratotomy to allow an increased level of accuracy as stated above depends upon another series of wound/healing events which are somewhat unpredictable (at least ±0.15 D).

Accordingly, there is a need for an intraocular lens which can be modified or enhanced once it is in place within the eye. There is also a need to be able to modify traditional intraocular lenses put in place following corneal transplant surgery.

Additionally, there is a need for an intraocular lens which can improve the current +/−0.75 D to 1.0 D refractive accuracy of IOL surgery to a desired +/−0.25 D.

Moreover, there is a further need for an IOL system which will allow the surgeon to postoperatively titrate the refraction after the patient's eye has healed from the initial surgery and the IOL position within the eye is stabilized.

Moreover, there is a need for an IOL system in which, in addition to being adjustable for spherical corrections, can accurately correct astigmatic errors, either congenital or induced, or which can include titratable cylindrical, multi-focal, bi-focal, tri-focal or predictable astigmatic corrections.

SUMMARY OF THE INVENTION

It is therefore an object of the present invention to provide a compound intraocular lens ("CIOL") which can be modified and enhanced once it is in place within the eye.

It is an additional object of the present invention to provide a CIOL which can be used to modify an existing IOL put in place following prior corneal transplant surgery, following prior IOL surgery, or to be used with the natural Crystalline lens of the eye (either in the normal condition or following a prior refractive surgery (e.g., corneal surgery)).

It is a further object of the present invention to provide a CIOL which can improve the refractive accuracy to +/−0.25 D.

Additionally, it is a further object of the present invention to provide a CIOL system which will allow the surgeon to postoperatively titrate the refraction after the initial surgery.

Furthermore, it is an object of the present invention to provide a CIOL wherein spherical, cylindrical, astigmatic, multi-focal, bi-focal, tri-focal or intended astigmatic correction is possible.

To achieve the objects and in accordance with the purpose of the invention, as embodied and broadly described herein, a compound intraocular lens for an eye comprises new designs of the cap and sandwich components of the MC-IOL.

This new CIOL (sandwich and cap lenses) could be attached to a previously-implanted base IOL of the type set forth in U.S. Pat. No. 5,222,981 or could be implanted over a previously implanted IOL. The new CIOL could be placed in the anterior chamber, placed in the posterior chamber (sulcus) or have a support member placed in the posterior chamber (sulcus) with a structural tab to hold the cap and sandwich lenses such that the sandwich and cap lenses rest in the anterior chamber (held in place by the support member placed in the sulcus with support elements projecting through the iris or around the pupillary border of the iris).

The accompanying drawings, which are incorporated in and constitute a part of this specification, illustrate one embodiment of the invention and, together with this invention, serve to explain the principles of the invention.

BRIEF DESCRIPTION OF THE DRAWINGS

FIG. 3A is a top view of the base lens of the MC-IOL;

FIG. 3B is a side view of the base lens of the MC-IOL;

FIG. 7A is a top view of sandwich lens of the CIOL of the present invention;

FIG. 7B is a side view of the sandwich lens of the CIOL of the present invention;

FIG. 8A is a top view of the fully-assembled (IOL of the present invention. FIG. 8B is a side view of the CIOL of FIG. 8A;

FIG. 9A is a top view of the posterior chamber support of the CIOL of the present invention;

FIG. 9B is a side view of the fully-assembled CIOL of the present invention;

FIG. 18A is a side view of the CIOL bonded to the crystalline lens in the posterior chamber;

DESCRIPTION OF THE PREFERRED EMBODIMENT

Figure 1A:
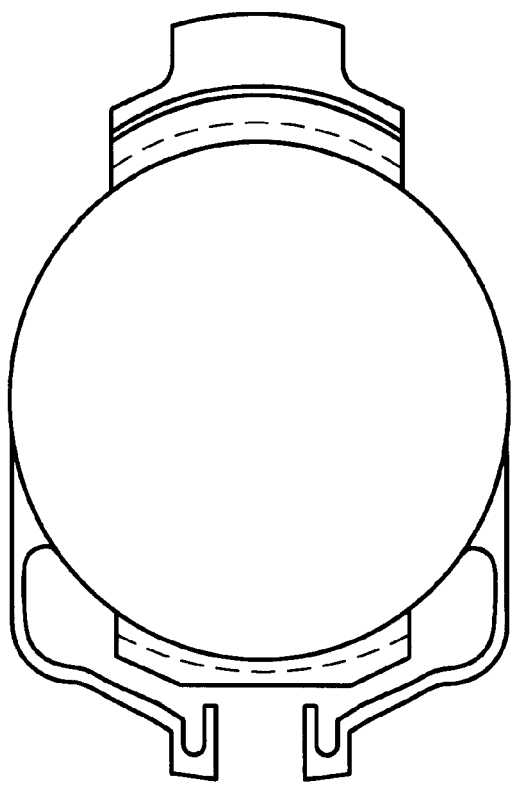
FIG. 1A is a top view of the cap lens of the prior multi-component IOL ("MC-IOL")

Reference will now be made in detail to the present preferred embodiment of the invention, an example of which is illustrated in the accompanying drawings in which like reference characters refer to corresponding elements.

The Multi-Component Intraocular Lens ("MC-IOL") as first disclosed in U.S. Pat. No. 5,222,981 ("the '981 patent"), represented a new concept in intraocular lens technology which allowed accurate surgical adjustment of the postoperative refractive state of the eye to achieve spectacle-free vision in virtually all patients. In contrast to the conventional, single, optical element IOL, the MC-IOL had three optical components: the Base lens which is permanently placed in the eye after the crystalline lens is removed (much like a conventional IOL) and the Sandwich and Cap lenses which attach to the Base lens so they can be easily removed and exchanged. See FIGS. 1–5 and 20–21. Alternative Sandwich and Cap lenses of different refractive powers allow the surgeon to modify and/or refine the final postoperative spherical and cylindrical refraction.

In an effort to analyze the problem of residual refractive errors after cataract surgery with preexisting IOL implants ("PCIOL"), several modifications of the MC-IOL concept were derived.

Figure 6A:
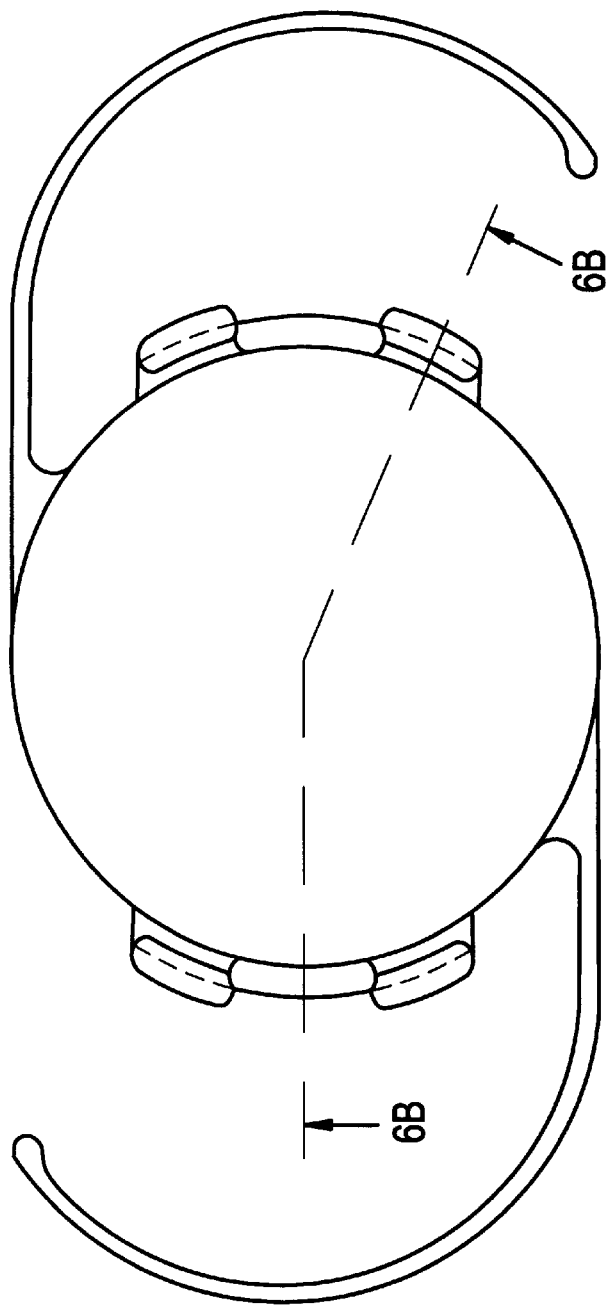
FIG. 6A is a top view of the cap lens of the CIOL of the present invention.
Figure 6B:
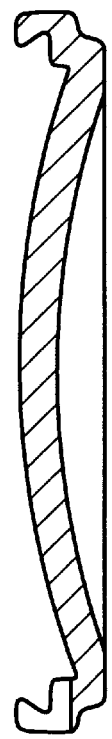
FIG. 6B is a side view of the cap lens of the CIOL of the present invention.
Figure 10:
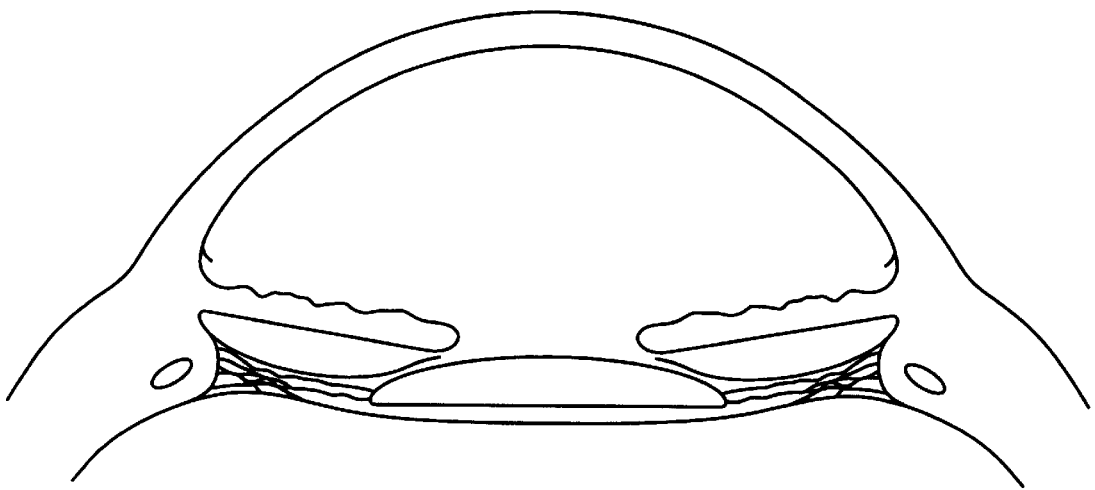
FIG. 10 is a side view of an eye after IOL surgery with a typical posterior chamber IOL in place.
Figure 11:
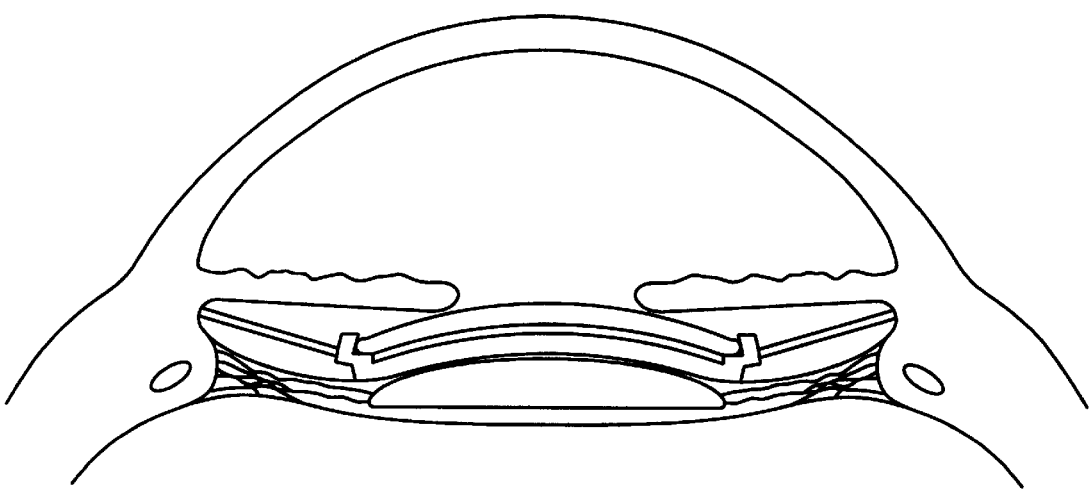
FIG. 11 is a side view of the CIOL in place with a posterior chamber IOL ("PCIOL") situated in the posterior chamber of the eye wherein the CIOL is supported by both the PCIOL and ociliary sulcus haptics.
Figure 12:
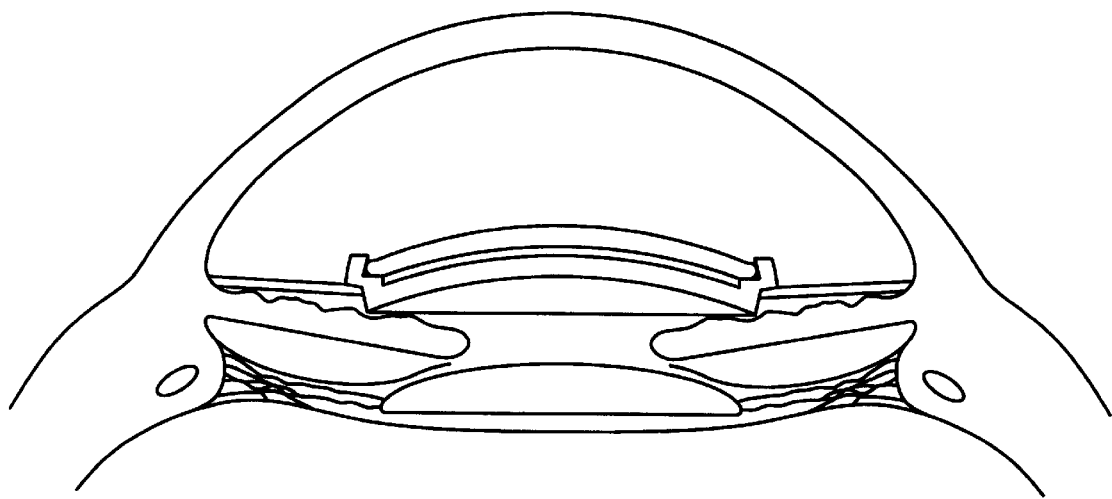
FIG. 12 is a side view of the CIOL in place situated in the anterior chamber with a posterior chamber IOL.
Figure 13:
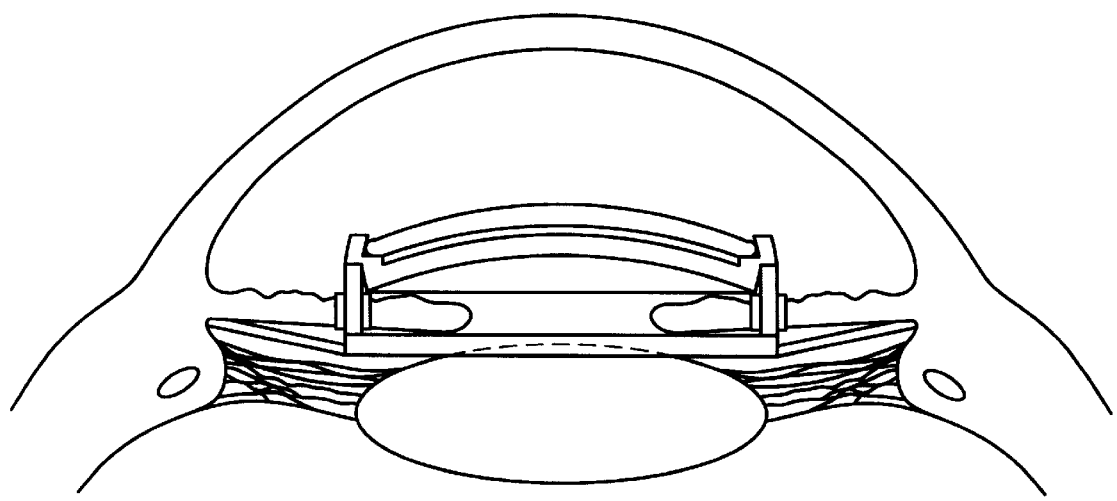
FIG. 13 is a side view of the CIOL situated with a support ring in the posterior chamber and the CIOL lens is situated in the anterior chamber.
Figure 14:
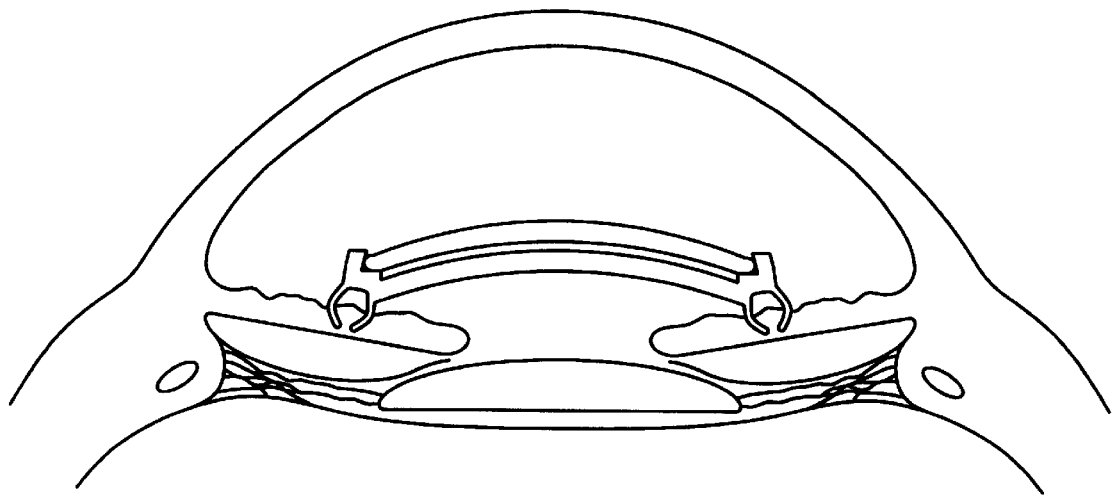
FIG. 14 is a side view of the CIOL attached to the iris with a posterior chamber IOL behind the iris.
Figure 14A:
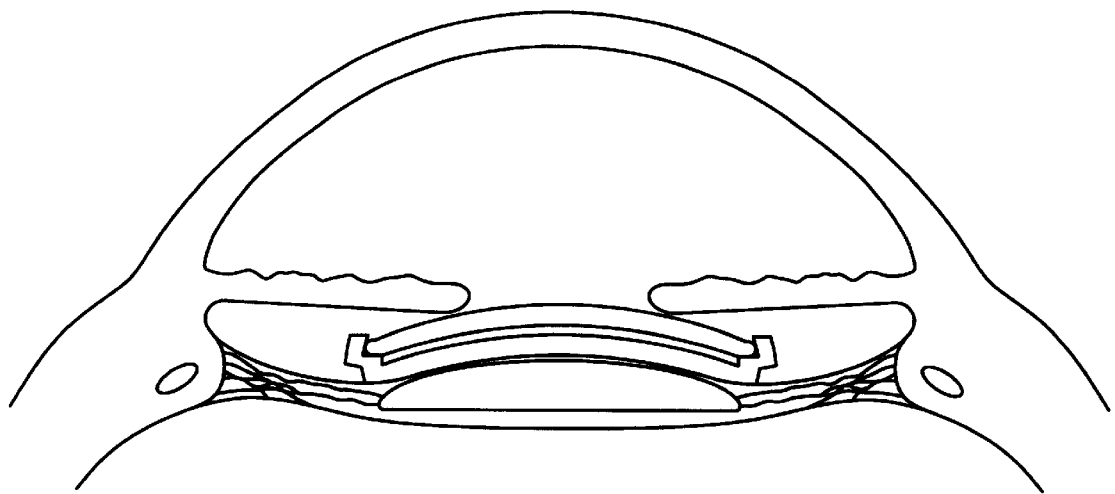
FIG. 14A is a side view showing the CIOL bonded to a supporting PCIOL in position in the posterior chamber.
Figure 15:
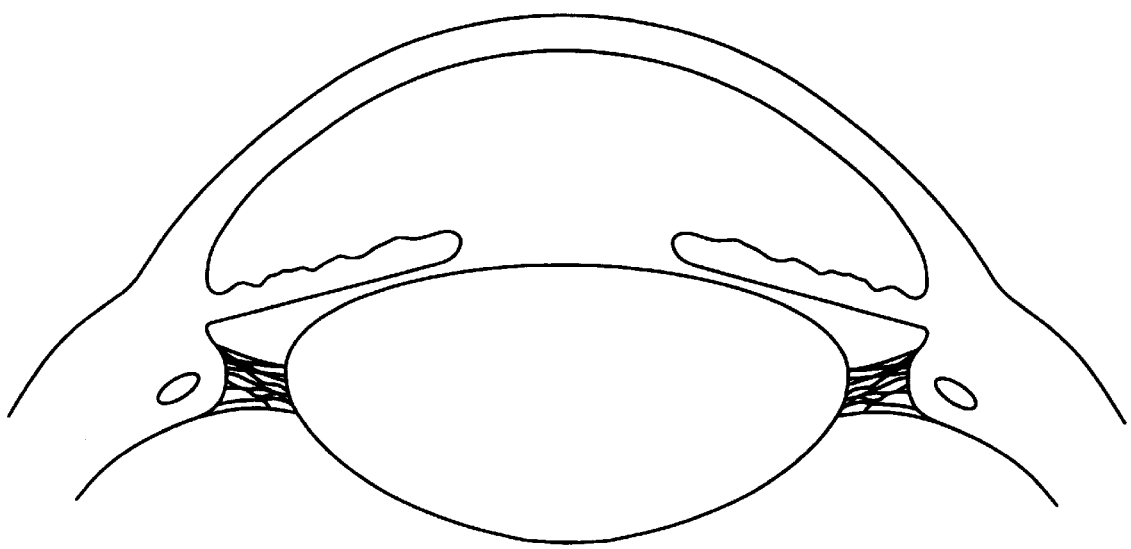
FIG. 15 is a side view of a crystalline lens in the eye.
Figure 16:
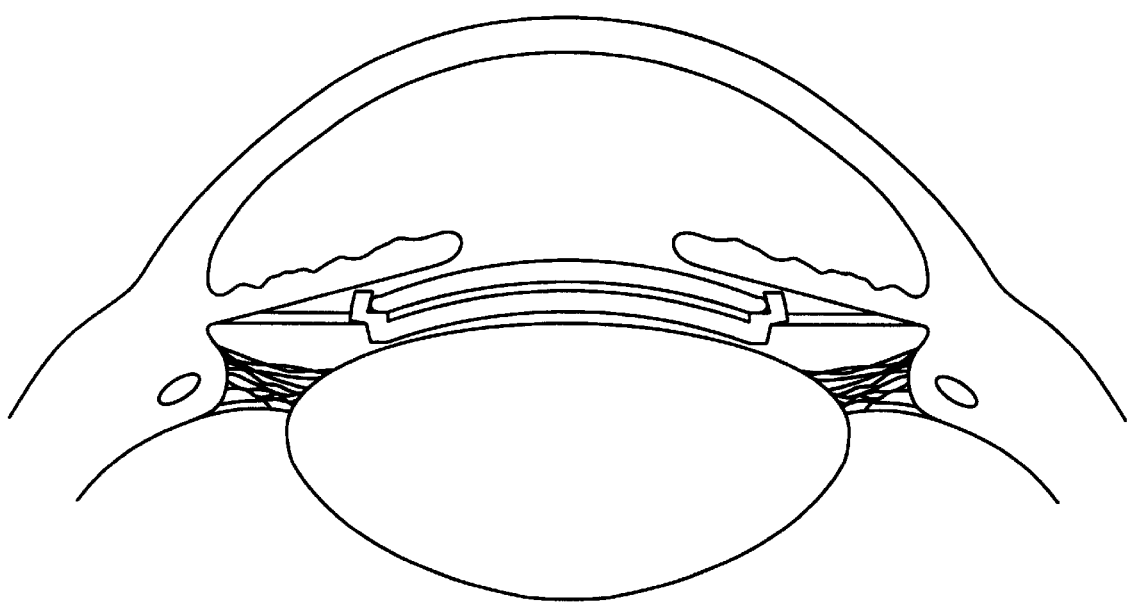
FIG. 16 is a side view of the CIOL positioned over the crystalline lens in the posterior chamber with ociliary sulcus support.
Figure 17:
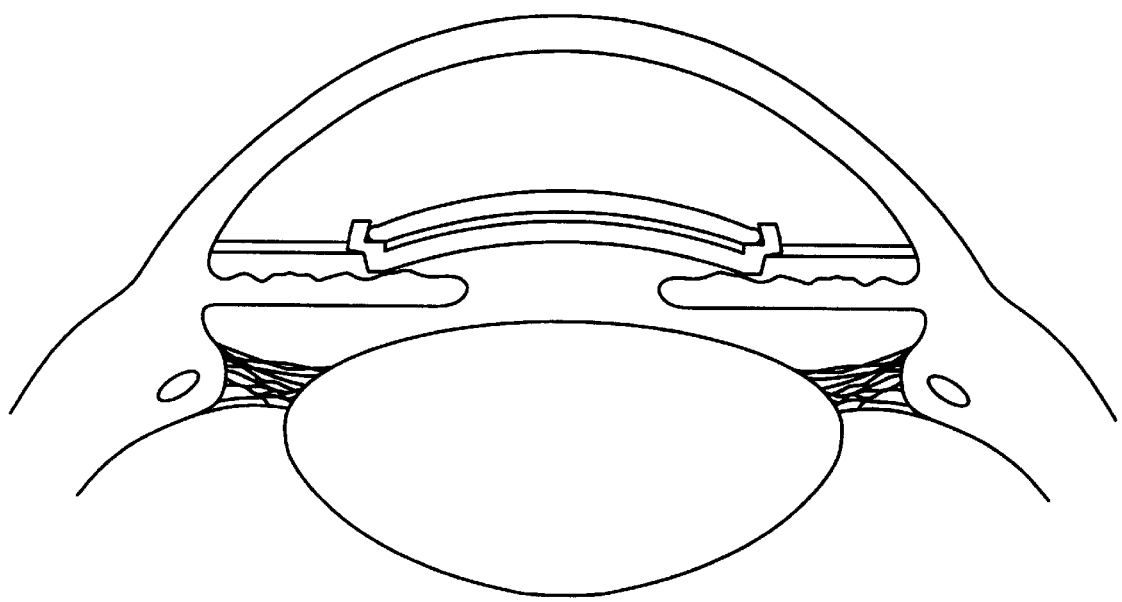
FIG. 17 is a side view of the CIOL positioned in the anterior chamber with the crystalline lens in the posterior chamber.
Figure 18:
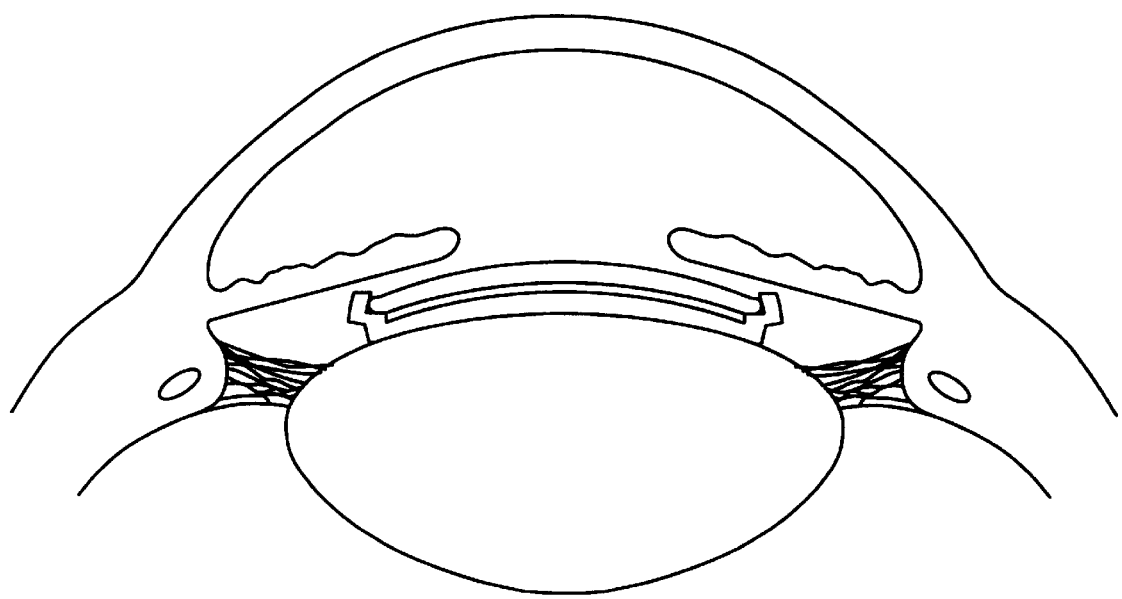
FIG. 18 is a side view of the CIOL lens fixated in the anterior chamber positioned over the crystalline lens.
Figure 19:
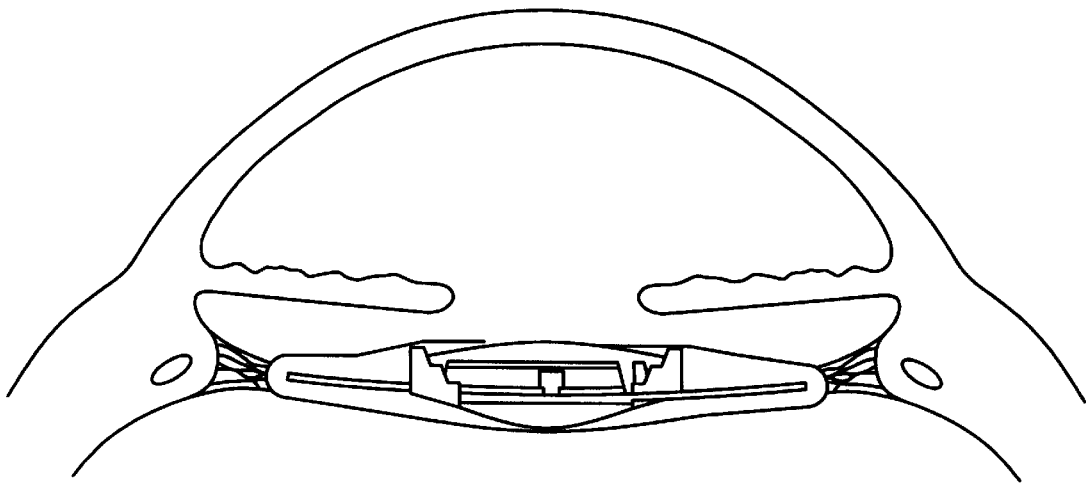
FIG. 19 is a side view of the MC-IOL assembly in the posterior chamber.
Figure 20:
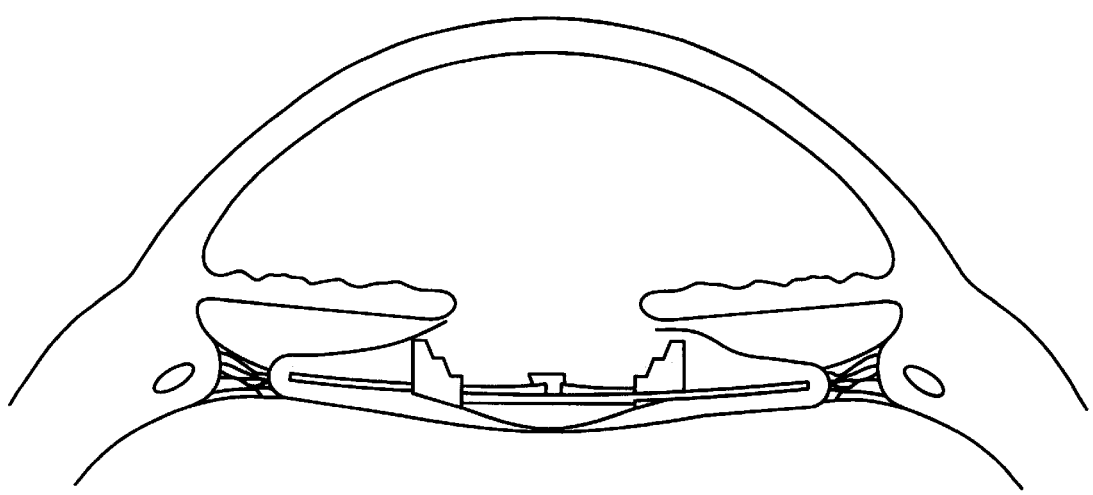
FIG. 20 is a side view of the MC-IOL with the base lens only positioned in the bag.
Figure 21B:
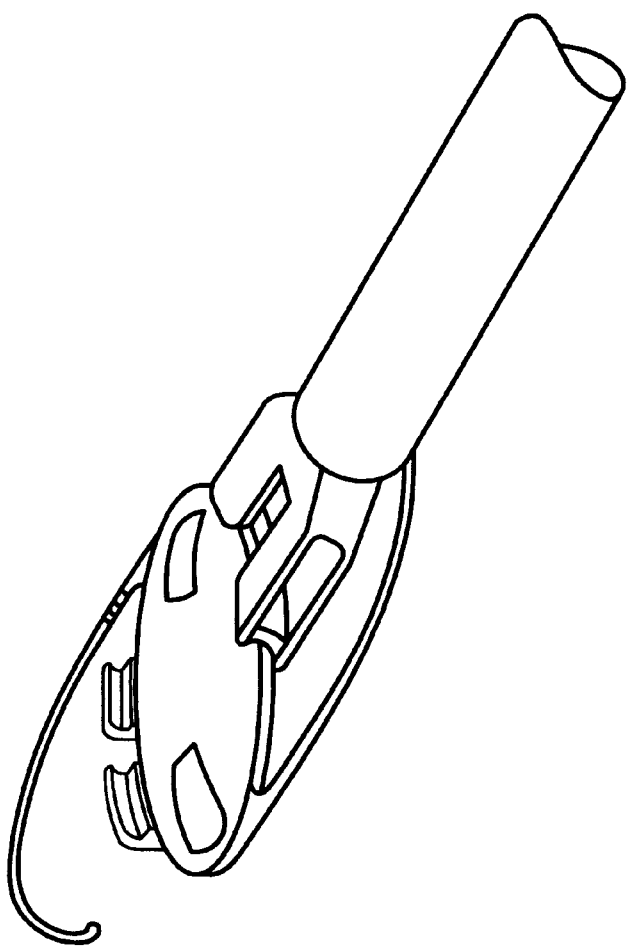
FIG. 21B is a side view of the tool for disassembly of the CIOL.
Figure 21D:
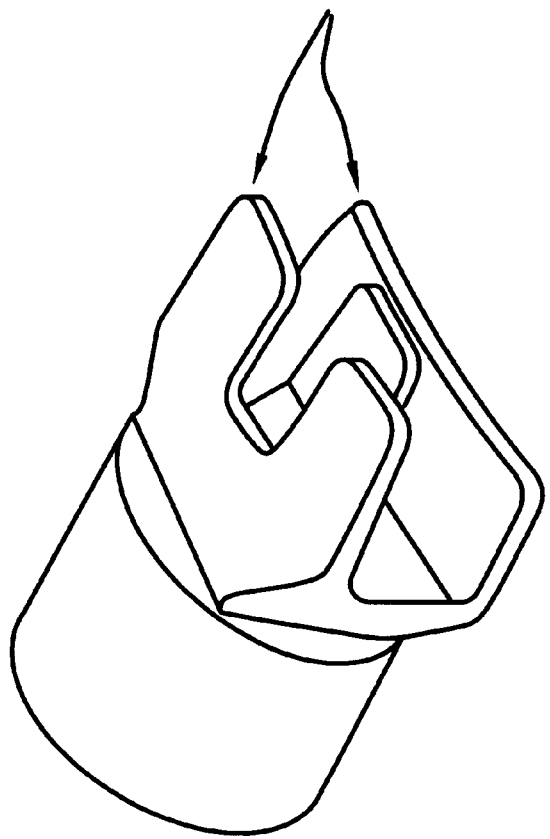
FIG. 21A is a side view of the installation tool used for installing the CIOL.
FIG. 21C is a side view of the IOL removal tool for removal of portions of the CIOL from the other portions of the assembly.
Figure 21E:
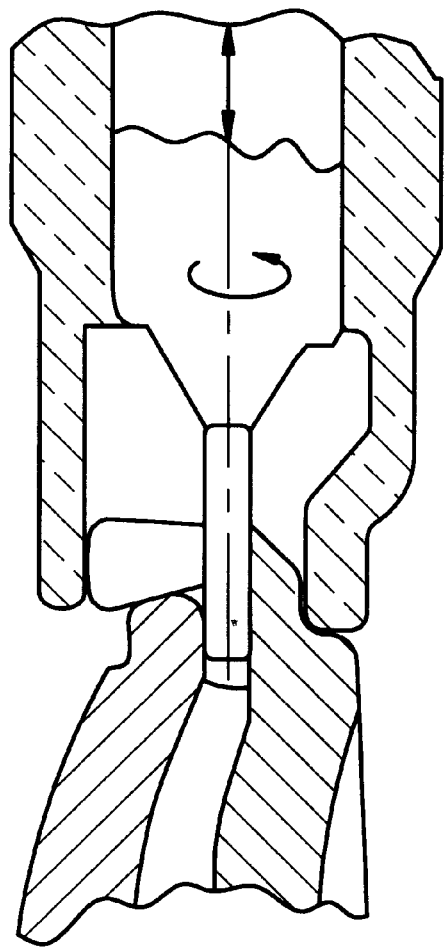
Figure 21C:
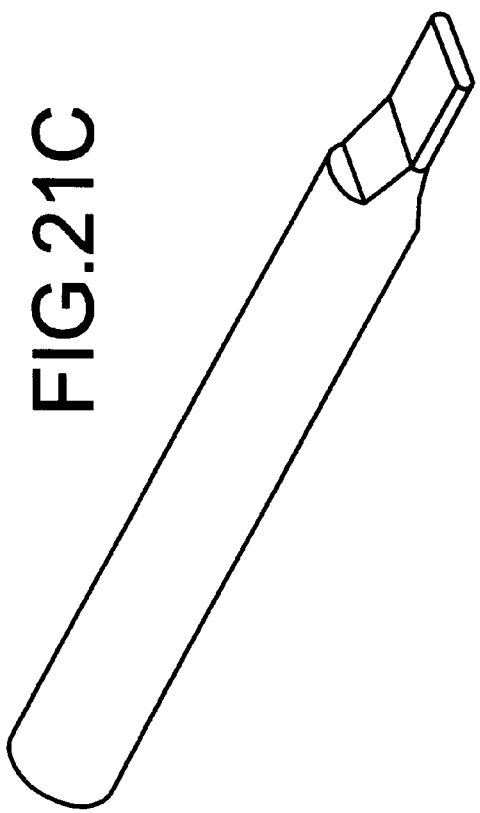

A new CIOL (i.e., an IOL comprised of two optical elements with or without an additional support element will be referred to as a compound IOL or "CIOL") (shown in FIGS. 1-2) could be attached to a previously-implanted MC-IOL base lens (FIG. 3) in a 2-stage surgical procedure if the refractive results of the primary surgery were less than desired. Alternatively, the new CIOL could be used with any preexisting posterior chamber IOL and placed (not attached) in the posterior chamber (sulcus) (as shown in FIG. 11), the anterior chamber (FIG. 12), bridging the anterior and posterior chambers (FIG. 1) or attached to the iris (FIG. 14). Finally, the new CIOL could be used with the crystalline lens and placed in the posterior chamber (sulcus) (FIG. 6), the anterior chamber (FIG. 17), bridging the anterior and posterior chambers (FIG. 13), or attached to the iris (FIG. 19).

In one case, the initially-implanted lens is the base lens of the original MC-IOL concept as set forth in the '981 patent. (FIGS. 20-21) It permanently heals into the posterior capsule and remains as a platform for the other two detachable refractive elements of the lens system. The refractive power of the Base lens is spherical (8.00 D to 14.00 D sphere in 2.00 D increments). Its plano-convex optical and mechanical design are similar to the currently used posterior chamber IOLs. (The base lens could have other curvatures, however.) The base lens (FIG. 3) may be comprised of polymethylmethacrylate ("PMMA"), acrylic or silicone and has a diameter of 6.00 mm, an optical aperture of 5.5 mm and can be implanted using a conventional 7.00 mm incision. Its haptics span 12.5 mm and are tilted by 15°. Its central thickness is approximately 0.5 mm. The Base lens has two machined slots with thicknesses of approximately 1.2 mm. These slots are designed to accept the second component lens and hold the assembly together. The base lens may also be comprised of materials which are capable of absorbing light in the ultraviolet wavelength portion of the light spectrum, between 380 and 389 nm. This feature would be advantageous because it would help in reducing glare, thereby enhancing vision capabilities. The base lens may also be tinted according to patient preference.

Attached to the Base lens are the two additional refractive elements of the CIOL. The middle lens, the Sandwich lens, shown in FIG. 2, carries the astigmatic (4.00 D sphere and 0.00 D to 4.00 D cylinder in 0.25 D increments) correction feature. The sandwich lens may be comprised of PMMA, acrylic or silicone and has a maximum central thickness of 0.4 mm, a diameter of 6.3 mm and an optical clear aperture of 5.5 mm. The sandwich lens may also be comprised of materials which are capable of absorbing light in the ultraviolet wavelength portion of the light spectrum. The sandwich lens may also have color or tinting added according to patient preference.

Figure 1B:
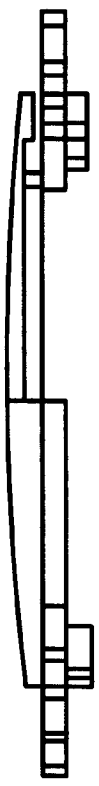
FIG. 1B is a side view of the cap lens of the prior MC-IOL.
Figure 2A:
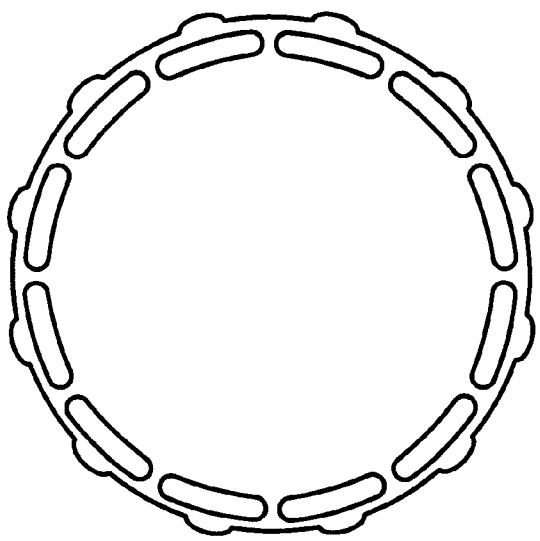
FIG. 2A is a top view of the sandwich lens of the MC-IOL.
Figure 2B:
FIG. 2B is a side view of the sandwich lens of the MC-IOL.
Figure 4:
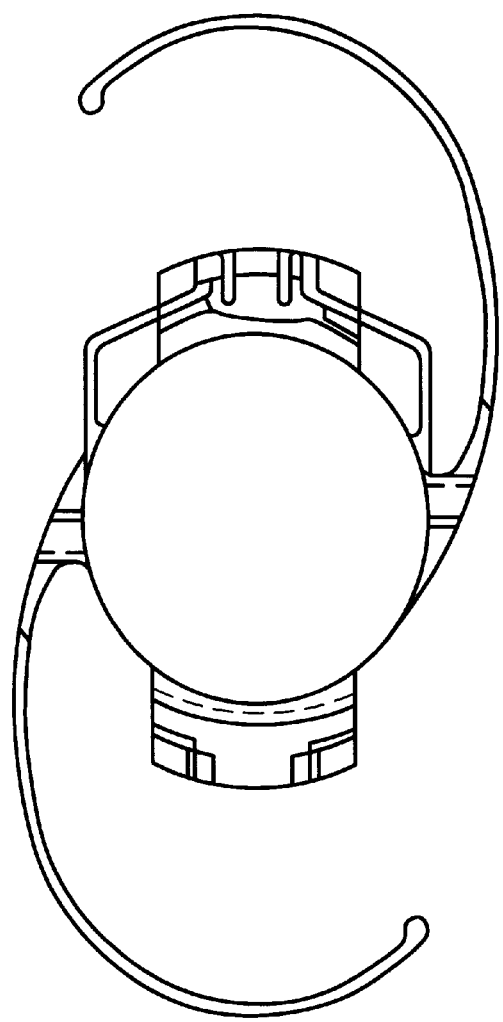
FIG. 4 is a top view of the fully-assembled MC-IOL.
Figure 5:
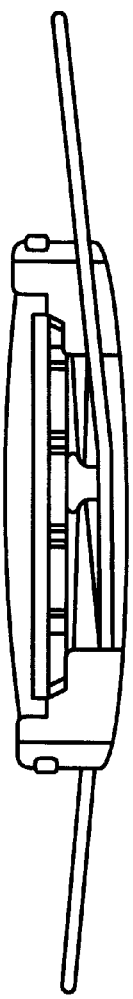
FIG. 5 is a side view of the fully-assembled MC-IOL.
Figure 5A:
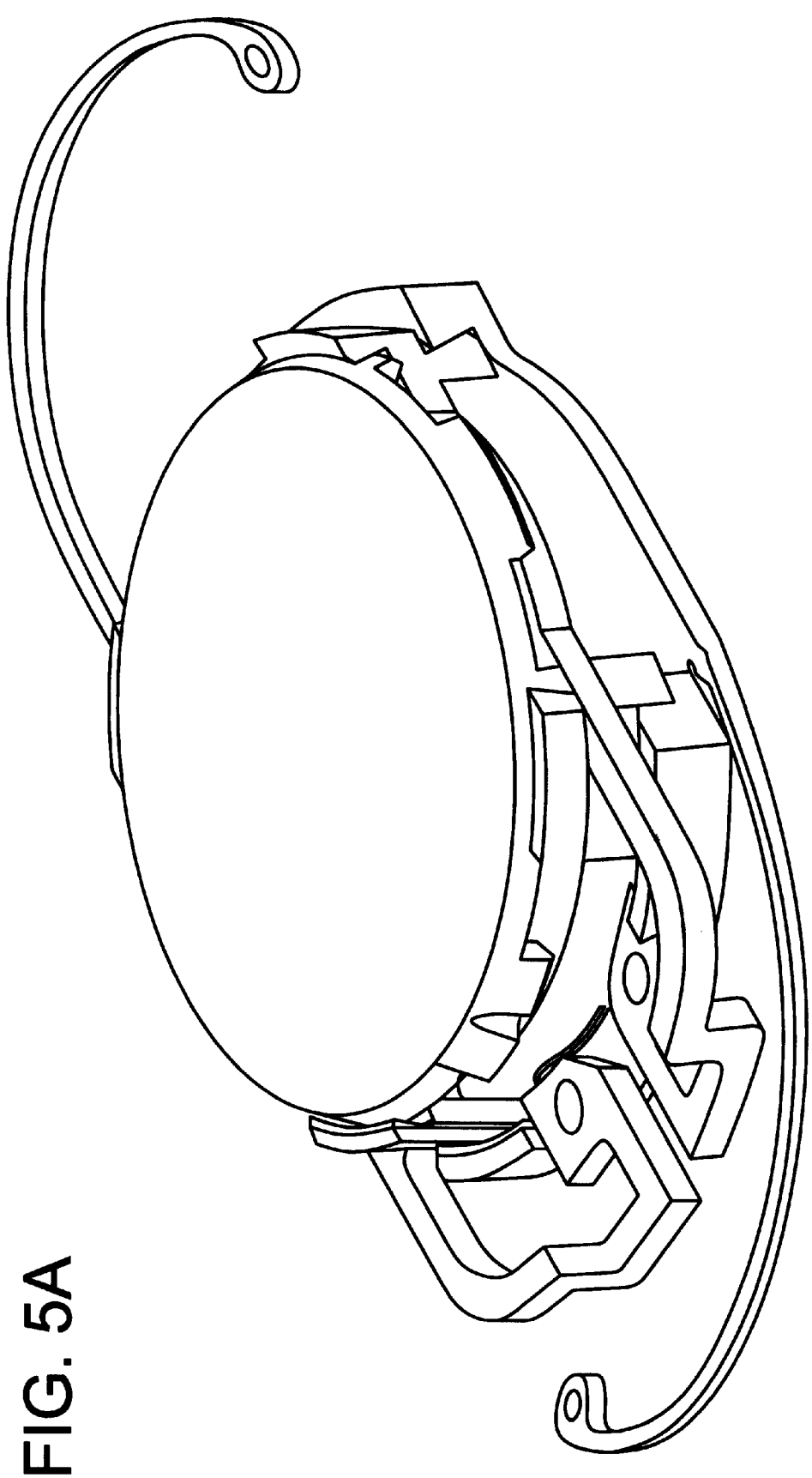
FIG. 5A is a top view of version 2 of the fully-assembled MC-IOL.
Figure 5B:
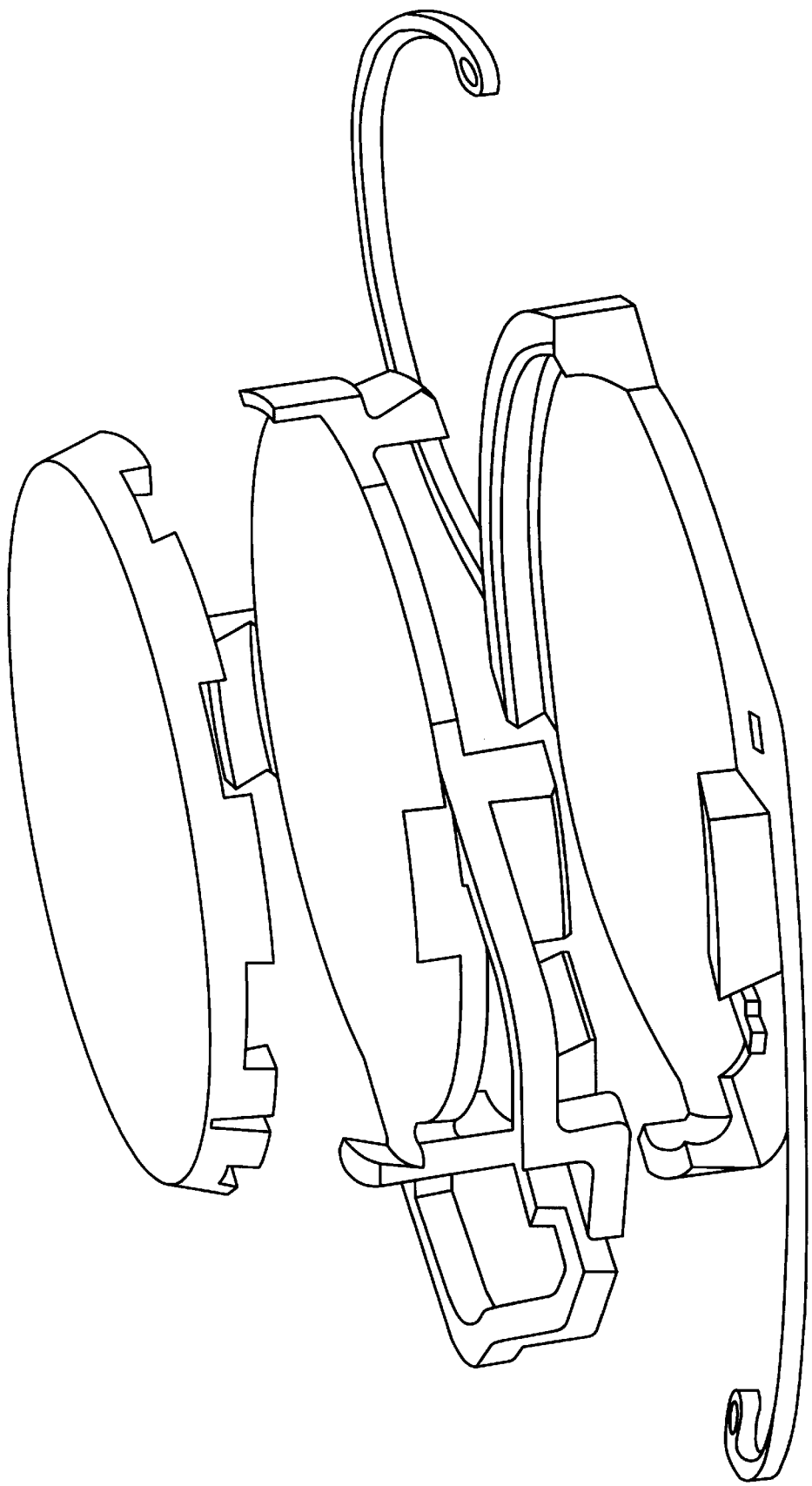
FIG. 5B is an exploded side view of version 2 of the MC-IOL.

As shown in FIG. 1, the Cap lens has additional spherical power (1.00 D to 9.50 D in 0.25 D increments) and may be either monofocal or multifocal. The cap lens may be comprised of PMMA, acrylic or silicone and is a plano-convex lens with a maximum central thickness of 0.3 mm, a diameter of 6.3 mm and an optical clear aperture of 5.5 mm. (The cap lens can also have other curvatures.) It has a tab and two small haptics which are used for attachment to the base lens. The cap lens may also be comprised of ultraviolet light absorbing materials and/or have tinting added.

The three piece system (i.e., the base lens of the MC-IOL (or a conventional IOL or crystalline lens of the eye plus the CIOL) has a spherical power range of 14.50 D and accuracy of +/−0.25 D (twice the accuracy of conventional IOLs). It has an adjustable cylindrical power of 4.00 D and adjustable spherical power of 3.0 D. Its maximum central thickness is 1.88 mm, the optical element diameter is 6.00 mm, and it has an optical aperture of 5.5 mm. The mass is 0.03 g and volume is 0.028 cm. The optical performance of the MC-IOL of the present invention at a resolution of 1001 p/mm the MTF is 0.61 compared with 0.55 for a conventional IOL.

The new modifications of the MC-IOL, also found in the CIOL concept, allow the cap and sandwich components described above to be used in conjunction with a previously-implanted posterior chamber IOL (conventional), or in conjunction with a previously-implanted base lens (MC-IOL disclosed in '981 patent) or in conjunction with the crystalline lens of the eye (see FIGS. 16–19). The crystalline lens or previously-implanted IOL would act (refractively) like the base lens of the MC-IOL (without attachment elements) in the '981 patent and the addition of the cap and sandwich lenses allows modification of sphere and cylinder in a second operative procedure to titrate the initial refractive result.

Any of the base, sandwich and/or cap components may be coated with chemicals to decrease their cellular reactivity such as heparin or other surface passivation techniques to prevent building of cellular debris at optical interface. Moreover, any of lens components may be configured with a multifocal corrective component of any of several varieties: derefractive or refractive, bull's eye or aspheric, depending upon the desired optical characteristics to be achieved. Additionally, extra components beyond the basic base, sandwich and cap components may be added to help with optical aberrations or other focusing refinements.

Specific predetermined combinations of lens powers for each of the three components may be utilized to achieve a large variety of possible corrective power while allowing only a minimum number of different lenses to be manufactured. These different combinations are set forth in Table A, for example, as would be true for the original MC-IOL concept. By placing small degrees of spherical correction in each of the three optical components, one can construct with a very limited inventory (about 55 lenses) all of the corrections needed to achieve optical powers from 13.0 D to 27.5 D of spherical correction and from 0 to 4.0 D of cylindrical correction in any axis, all in 0.25 D steps. Therefore, a surgeon will have an inventory of lens components available which will allow for the construction of virtually any common spherical and/or astigmatic correction.

The system design takes into account the realistic tolerances achieved in a modern IOL manufacturing operation. Given current technology, the production of these lens components is roughly equivalent to manufacturing three single piece IOLs. Thus, multi-compound IOL's of the present invention need not be custom-manufactured for a particular patient. A surgeon can have a ready inventory of lenses on hand and merely utilize them in a particular combination to achieve the desired correction.

Special tools and attachment/detachment procedures have been designed for utilization with the compound IOL of the present invention (See FIGS. 22A–22C). For example, a specially-modified forceps, shown in FIG. 22A, has been designed for use in attaching the cap lens/sandwich lens components of the CIOL to the base lens. The lever is squeezed to grip the lens component to attach it to the base lens. The disassembly tool, shown in FIG. 22B, has top and bottom flanges which fit over the CIOL retainers to prevent rotation of the cap lens while the flat blade of the tool is inserted into the space between the tabs and the lenses. The flat blade is then rotated causing it to lift the sandwich lens and free it from the restraints. The removal tool shown in FIG. 22C is utilized by slipping the flat blade between the cap and sandwich lenses at the space between the retainers on the cap lens. The blade is then rotated to force the lenses apart.

The surgical procedure involved in the primary operation where the crystalline lens is to be removed is completely analogous to routine phacoemulsification surgery with implantation of a posterior chamber IOL through a 7.00 mm incision, if PMMA rigid materials are to be used, smaller incisions are possible if foldable materials are to be used. Once the Base lens has been implanted, the Cap and Sandwich lens assembly is intraoperatively affixed by the surgeon to the Base lens. The Cap and Sandwich lens assembly is performed outside the eye; the Sandwich lens is oriented to the appropriate astigmatic axis based on the preoperative estimation of the anticipated postoperative astigmatic correction.

Once the refractive stability has been observed after the initial surgical procedure, the refractive state of the eye dictates whether or not an enhancement is necessary. If the residual refraction is significant, both spherical and astigmatic corrections can be adjusted based on the residual refractive status of the eye. Alternatively, if a patient has been given a multifocal lens and is not comfortable with the quality of vision achieved, the multifocal Cap lens component can be exchanged for a monofocal Cap lens component to rectify the situation. This system can also be used to induce specific degrees of astigmatism to allow increased depth of focus to act as pseudo-accommodation. The second operative procedure consists of opening the original surgical wound, detaching the original Cap and Sandwich lens components, and interchanging them with new Cap and Sandwich lens components with the Sandwich lens oriented according to the appropriate preoperative refractive data. The wound is then closed and assembly completed within the eye. Using the same wound from the initial enhancement procedure assures that the would healing properties of the eye will be consistent between the first and the second operations.

Armlike tab mechanisms may be used on the cap which fit into cuts made in the base lens for attachment of the cap to base. Alternatively, tabs can be formed in more of a sheet or plate configuration rather than arm to allow a more interlocking attachment. A specially-modified forceps, shown in FIGS. 22A–22E, has been designed for use in the attachment procedure. The forceps has a slotted teethlike arrangement on the ends which can be dropped into the tab opening to grab onto the base lens.

Or, if you have a situation where you need to modify a pre-existing IOL implant, where the implant has to serve as the Base lens, the physician's task is to add to this preexisting IOL implant, spherical and astigmatic lens components which can modify any residual postoperative refraction.

There are two techniques which can be used to accomplish this task. In the first scenario, the cap and sandwich lens components could be assembled outside of the eye or, if foldable elements are used, assembled inside the eye and then would be placed in the posterior chamber behind the iris overlying the existing implanted IOL.

Alternatively, a flange with posts projecting through the iris would be placed into the posterior chamber overlying the previously-implanted IOL. The posts would project vertically towards the cornea and small irredectomies would be used to expose the posts in the anterior chamber. These posts would then be similar to the posts of the Base lens of the original MC-IOL and could then be used to attach the cap and sandwich lenses.

The advantage of the CIOL of the present invention is that it allows the surgeon to deliver a refractive result which is comparable to preoperative eyeglass or contact lens correction in virtually every case. The patient can also be assured that, if the initial surgical result is not accurate enough, an enhancement operative procedure with minimal additional risk can modify the initial surgical result so that the end refractive status of the eye will be close to emmetropia. Also, the patient can try new technology, such as multifocal lenses, as new technologies are developed or become available. If results are unsatisfactory (immediately postoperatively or years later) an exchange of the refractive element can also be accomplished, returning the patient to a monofocal vision. In addition, various types of telescopic lens combinations for macular degeneration could conceivably be introduced at some later date using the initial surgical platform and interchangeable lens elements.

From a surgeon's perspective, the ability to control the outcome independent of biological variables is a significant improvement over prior technology. In addition, the surgical technique involved with these procedures is very similar to routine cataract surgery, which virtually all ophthalmologists are comfortable with. Similarly, all the materials, technology and instrumentation are well within the grasp of most ophthalmic surgeons.

It will be apparent to those skilled in the art that various modifications and variations can be made in the compound intraocular lens of the present invention without departing from the scope or spirit of the invention. Thus, it is intended that the present invention cover the modifications and variations of this invention provided they come within the scope of the appended claims and their equivalents.

What is claimed is:

1. A compound intraocular lens system for an eye comprising:
   an existing lens placed in the eye;
   a cap lens situated on said existing lens and having a plurality of attachment elements on an anterior surface of said caps lens, wherein the cap lens is coated with a chemical material to decrease the cellular reactivity of such cap lens; and
   an attachable/detachable sandwich lens which clips into said attachment elements of said cap lens.

2. The compound intraocular lens system as claimed in claim 1 wherein the sandwich lens is comprised of PMMA.

3. The compound intraocular lens system as claimed in claim 1 wherein the sandwich lens is comprised of acrylic.

4. The compound intraocular lens system as claimed in claim 1 wherein the sandwich lens is comprised of silicone.

5. The compound intraocular lens system as claimed in claim 1 wherein the sandwich lens is comprised of glass.

6. The compound intraocular lens system as claimed in claim 1 wherein the sandwich lens is comprised of any combination of PMMA, acrylic, silicone or glass materials.

7. The compound intraocular lens system as claimed in claim 1 wherein the sandwich lens is comprised of a material which is capable of absorbing light in the ultraviolet portion of the light spectrum.

8. The compound intraocular lens system as claimed in claim 1 wherein the sandwich lens is coated with a chemical material to decrease the cellular reactivity of such sandwich lens.

9. The compound intraocular lens system as claimed in claim 1 wherein the sandwich lens is surface-treated by passivation to decrease the cellular reactivity of such sandwich lens.

10. The compound intraocular lens system as claimed in claim 8 wherein the chemical material is heparin.

11. The compound intraocular lens system as claimed in claim 1 wherein the existing lens is a conventional posterior chamber intraocular lens which has permanently healed in the eye after a first surgical event and is used as a platform for the other two components.

12. The compound intraocular lens system as claimed in claim 1 wherein the existing lens is a base lens of a multicomponent intraocular lens which has permanently healed in the posterior chamber of the eye after a first surgical event and is used as a platform for the other two components.

13. The compound intraocular lens system as claimed in claim 1 wherein the compound intraocular lens system is situated in the anterior chamber of the eye.

14. The compound intraocular lens system as claimed in claim 1 wherein the compound intraocular lens system is configured to be attached to the iris of the eye.

15. The compound intraocular lens system as claimed in claim 12 wherein the base lens is comprised of PMMA.

16. The compound intraocular lens system as claimed in claim 12 wherein the base lens is comprised of acrylic.

17. The compound intraocular lens system as claimed in claim 12 wherein the base lens is comprised of silicone.

18. The compound intraocular lens system as claimed in claim 12 wherein the base lens is comprised of glass.

19. The compound intraocular lens system as claimed in claim 12 wherein the base lens is comprised of any combination of PMMA, acrylic, silicone or glass materials.

20. The compound intraocular lens system as claimed in claim 12 wherein the base lens is comprised of a material which is capable of absorbing light in the ultraviolet portion of the light spectrum.

21. The compound intraocular lens system as claimed in claim 12 wherein the base lens is coated with a chemical material to decrease the cellular reactivity of such base lens.

22. The compound intraocular lens system as claimed in claim 12 wherein the base lens is surface-treated by passivation to decrease the cellular reactivity of such base lens.

23. The compound intraocular lens system as claimed in claim 21 wherein said chemical material is heparin.

24. The compound intraocular lens system as claimed in claim 1 wherein the cap lens is comprised of PMMA.

25. The compound intraocular lens system as claimed in claim 1 wherein the cap lens is comprised of acrylic.

26. The compound intraocular lens system as claimed in claim 1 wherein the cap lens is comprised of silicone.

27. The compound intraocular lens system as claimed in claim 1 wherein the cap lens is comprised of glass.

28. The compound intraocular lens system as claimed in claim 1 wherein the cap lens is comprised of any combination of PMMA, acrylic, silicone or glass materials.

29. The compound intraocular lens system as claimed in claim 1 wherein the cap lens is comprised of a material which is capable of absorbing light in the ultraviolet portion of the light spectrum.

30. The compound intraocular lens system as claimed in claim 1 wherein the cap lens is coated with a chemical material to decrease the cellular reactivity of such cap lens.

31. The compound intraocular lens system as claimed in claim 1 wherein the cap lens is surface-treated by passivation to decrease the cellular reactivity of such cap lens.

32. The compound intraocular lens system as claimed in claim 30 wherein the chemical material is heparin.

33. The compound intraocular lens system as claimed in claim 12 wherein the base lens has a monofocal capacity with a spherical refractive power of + or –.

34. The compound intraocular lens system as claimed in claimed in claim 12 wherein the base lens has a multifocal capacity.

35. The compound intraocular lens system as claimed in claim 12 wherein the base lens is comprised of an astigmatic correction feature.

36. The compound intraocular lens system as claimed in claim 12 wherein the base lens has a bifocal capacity.

37. The compound intraocular lens system as claimed in claim 4 wherein the base lens has a trifocal capacity.

38. The compound intraocular lens system as claimed in claim 12 wherein the base lens has any combination of monofocal, bifocal, trifocal, multifocal or astigmatic corrective optical properties.

39. The compound intraocular lens system as claimed in claim 1 wherein the cap lens has a monofocal capacity with a spherical refractive power of + or –.

40. The compound intraocular lens system as claimed in claim 1 wherein the cap lens has a multifocal capacity.

41. The compound intraocular lens system as claimed in claim 1 wherein the cap lens is comprised of an astigmatic correction feature.

42. The compound intraocular lens system as claimed in claim 1 wherein the cap lens has a bifocal capacity.

43. The compound intraocular lens system as claimed in claim 1 wherein the cap lens has a trifocal capacity.

44. The compound intraocular lens system as claimed in claim 1 wherein the cap lens has any combination of monofocal, bifocal, trifocal, multifocal or astigmatic corrective optical properties.

45. The compound intraocular lens system as claimed in claim 1 wherein the sandwich lens has a monofocal capacity with a spherical refractive power of + or–.

46. The compound intraocular lens system as claimed in claim 1 wherein the sandwich lens has a multifocal capacity.

47. The compound intraocular lens system as claimed in claim 1 wherein the sandwich lens is comprised of an astigmatic correction feature.

48. The compound intraocular lens system as claimed in claim 1 wherein the sandwich lens has a bifocal capacity.

49. The compound intraocular lens system as claimed in claim 1 wherein the sandwich lens has a trifocal capacity.

50. The compound intraocular lens system as claimed in claim 1 wherein the sandwich lens has any combination of monofocal, bifocal, trifocal, multifocal or astigmatic corrective optical properties.

51. The compound intraocular lens system as claimed in claim 12 wherein the power of the base lens is 8.00 D to 14.00 D.

52. The compound intraocular lens system as claimed in claim 12 wherein the base lens has a diameter of 6.00 mm and an optical aperture of 5.5 mm.

53. The compound intraocular lens system as claimed in claim 1 wherein the sandwich lens has a diameter of 6.3 mm and an optical aperture of 5.5 mm.

54. The compound intraocular lens system as claimed in claim 1 wherein the cap lens has a diameter of 6.3 mm and an optical aperture of 5.5 mm.

55. The compound intraocular lens system as claimed in claim 1 wherein the system has a spherical power range of 14.5 OD.

56. The compound intraocular lens system as claimed in claim 1 wherein the system has a vision correction accuracy of +/–0.25 OD.

57. The compound intraocular lens system as claimed in claim 1 wherein the system has an adjustable cylindrical power of 4.0 OD.

58. The compound intraocular lens system as claimed in claim 1 wherein the system has an adjustable spherical power of 3.0 OD.

59. A compound intraocular lens system for an eye comprising:
   an existing lens placed in the eye;
   a cap lens situated on said existing lens and having a plurality of attachment elements on an anterior surface of said caps lens, and
   an attachable/detachable sandwich lens which clips into said attachment elements of said cap lens, wherein said existing lens is a base lens of a multicomponent intraocular lens which has permanently healed in the posterior chamber of the eye after a first surgical event and is used as a platform for the cap lens and sandwich lens, and wherein said base lens is coated with a chemical material to decrease the cellular reactivity of such base lens.

60. A compound intraocular lens system for an eye comprising:
   an existing lens placed in the eye;
   cap lens situated on said existing lens and having a plurality of attachment elements on an anterior surface of said caps lens, and
   an attachable/detachable sandwich lens which clips into said attachment elements of said cap lens, wherein the sandwich lens is coated with a chemical material to decrease the cellular reactivity of such sandwich lens.

61. A multi-component intraocular lens systems for an eye, comprising:
   a base intraocular lens, for positioning in the eye, said base intraocular lens having a radius and a circumference and including a first plurality of flanges selectively interspersed around said circumference, and a first plurality of projections for holding said multi-component intraocular lens system in place in the eye;
   a cap lens situated on said base lens, said cap lens having a radius and a circumference and including a second plurality of flanges, a first subset of said second plurality of flanges projecting upwards from said cap lens and a second subset of said second plurality of flanges projecting downwards from said cap lens, both of said first and second subsets of said second plurality of flanges being selectively interspersed around said circumference of said cap lens; and
   a sandwich lens, fixed to an anterior surface of said cap lens, said sandwich lens having a radius and a circumference and including a third plurality of flanges projecting downwards from said sandwich lens and being oriented in such a manner as to interlockingly engage with said second plurality of flanges so as to securely hold said sandwich lens in the correct orientation for appropriate correction of vision of said eye.

62. A multi-component intraocular lens system for an eye, comprising:

a base intraocular lens, for positioning in the eye, said base intraocular lens having a radius and a circumference and including a first plurality of flanges selectively interspersed around said circumference, and a first plurality of projections for holding said multi-component intraocular lens system in place in the eye;

a sandwich lens situated on said base lens, said sandwich lens having a radius and a circumference and including a second plurality of flanges, a first subset of said second plurality of flanges projecting upwards from said sandwich lens and a second subset of said second plurality of flanges projecting downwards from said sandwich lens, both of said first and said second subsets of said second plurality of flanges being selectively interspersed around said circumference of said sandwich lens; and a cap lens, situated on said sandwich lens, said cap lens having a radius and a circumference and including a third plurality of flanges projecting downwards from said cap lens and being oriented in such a manner as to interlockingly engage with said second plurality of flanges so as to securely hold said cap lens in the correct orientation for appropriate correction of vision of said eye.

\* \* \* \* \*